United States Patent [19]

Grossmann et al.

[11] Patent Number: 4,545,371
[45] Date of Patent: * Oct. 8, 1985

[54] SYSTEM AND METHOD FOR BANDAGING A PATIENT

[75] Inventors: Frederic Grossmann, Lake Forest, Ill.; Larry A. Sims, Hermosa Beach, Calif.

[73] Assignee: American Hospital Supply Corporation, Evanston, Ill.

[*] Notice: The portion of the term of this patent subsequent to Feb. 22, 2000 has been disclaimed.

[21] Appl. No.: 589,867

[22] Filed: Mar. 19, 1984

Related U.S. Application Data

[63] Continuation of Ser. No. 460,086, Jan. 21, 1983, abandoned, which is a continuation of Ser. No. 186,352, Sep. 11, 1980, abandoned.

[51] Int. Cl.⁴ .............................................. A61F 13/00
[52] U.S. Cl. ................................. 128/132 D; 128/155; 128/156
[58] Field of Search ..................... 128/132 D, 155, 156

[56] References Cited

U.S. PATENT DOCUMENTS

| | | | |
|---|---|---|---|
| 3,260,260 | 7/1966 | Questel | 128/132 |
| 3,299,890 | 1/1967 | Parker | 128/156 |
| 3,349,765 | 10/1967 | Blanford | 128/132 |
| 4,374,520 | 2/1983 | Grossmann et al. | 128/132 D |

OTHER PUBLICATIONS

Op Site Bandage Wrapper Instructions.
Publication: Instructions for Use-Op-Site Bandage.

*Primary Examiner*—C. Fred Rosenbaum
*Assistant Examiner*—Sherri E. Vinyard
*Attorney, Agent, or Firm*—Donald L. Barbeau

[57] ABSTRACT

A system for applying relatively large adhesive backed bandages to a patient for a wound dressing, burn dressing, surgical incise drape, etc. The system includes an applicator handle that is substantially less flexible than the bandage, which is joinable to the bandage during application, but which is removed from the bandage so as not to interfere with the flexible functioning of such bandage on a patient's anatomy.

7 Claims, 14 Drawing Figures

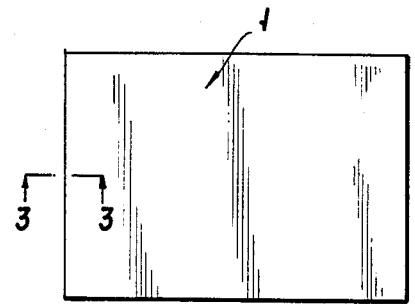 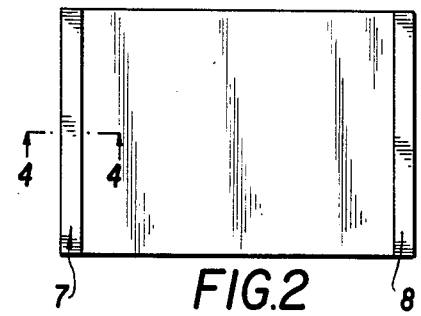 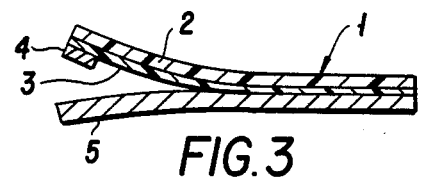 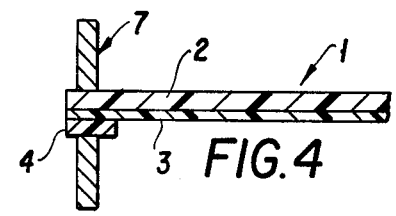 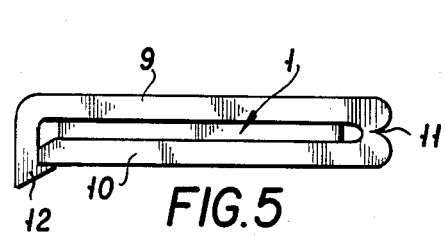 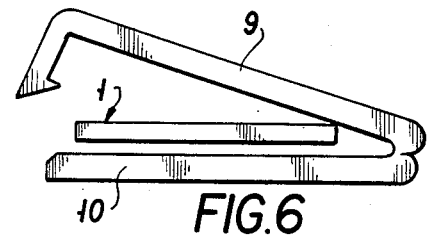 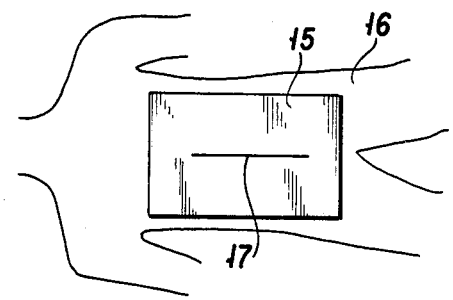

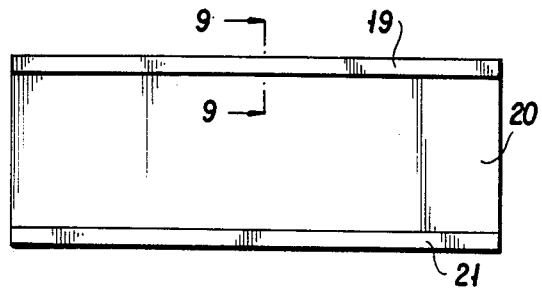
FIG. 8
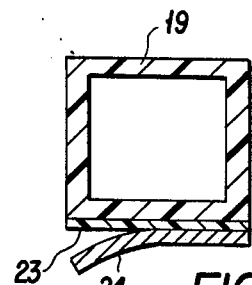
FIG. 9
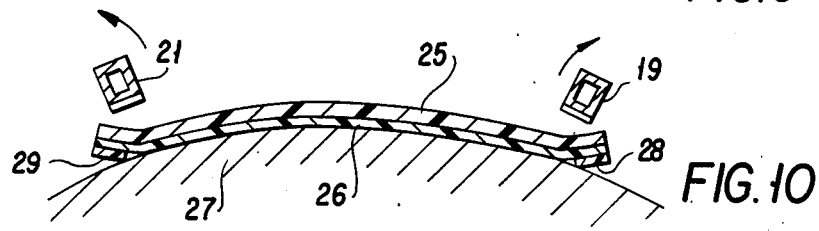
FIG. 10
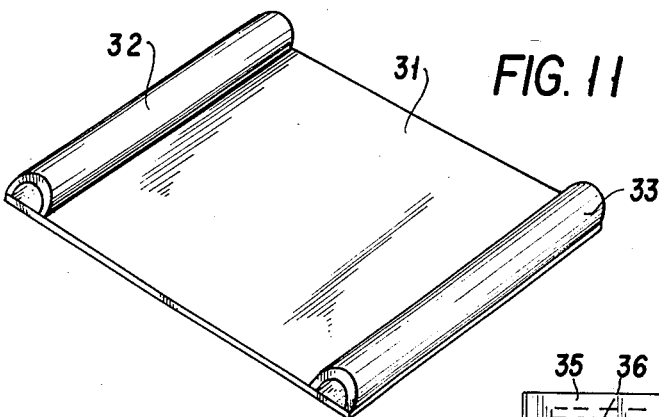
FIG. 11
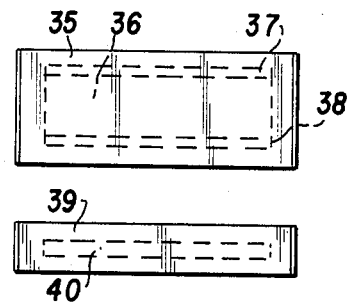
FIG. 13
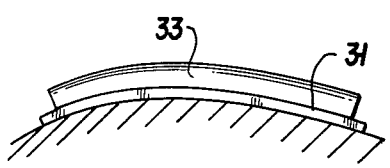
FIG. 12
FIG. 14

SYSTEM AND METHOD FOR BANDAGING A PATIENT

This application is a continuation of Ser. No. 460,086, filed Jan. 21, 1983, now abandoned, which is a continuation of Ser. No. 186,352, filed Sept. 11, 1980, now abandoned.

BACKGROUND

There has been a substantial problem in applying large area adhesive backed bandages to patients. Such bandages might be used for a surgical drape, such as shown in U.S. Pat. No. 3,236,370. There is considerable difficulty in keeping the large area drapes from sticking to themselves or from wrinkling during the application procedure. Often several nurses or physicians are required to apply such surgical incise drapes. The drape is called an "incise" drape when a surgical incision is made directly through the drape. Similar problems exist with other relatively large area bandages for wounds or burns.

One type of adhesive backed bandage having a relatively large area making it difficult to handle is a vapor permeable, bacteria impermeable transparent bandage manufactured by the British firm of Smith & Nephew, Ltd. and marketed in the United States under the OP-SITE trademark. This OP-SITE bandage has had considerable problems because of its extremely flexible nature and tacky adhesive that tends to stick to itself and wrinkle if not very carefully handled when applied to a patient.

SUMMARY OF THE INVENTION

The present invention overcomes the above problems by providing an applicator handle that is joined to the bandage while such bandage is being applied to the patient, and this applicator handle is removed after the bandage has been applied so the bandage can be smoothly contoured to the patient's anatomy. Such applicator handle can be mechanically or adhesively secured to the bandage.

THE DRAWINGS

FIG. 1 is a top plan view of the flexible bandage;

FIG. 2 is a top plan view of the flexible bandage with two applicator handles of a first embodiment attached;

FIG. 3 is an enlarged sectional view taken along line 3—3 of FIG. 1;

FIG. 4 is an enlarged sectional view taken along line 4—4 of FIG. 2;

FIG. 5 is a left end view of FIG. 4 showing a clamp type handle in closed condition;

FIG. 6 is a view similar to FIG. 5, but showing the clamp type handle in open condition;

FIG. 7 is a schematic showing of a patient with an incise drape;

FIG. 8 is a top plan view of a second embodiment of a handle attached to the flexible bandage;

FIG. 9 is an enlarged sectional view taken along line 9—9 of FIG. 8;

FIG. 10 is a sectional view of the flexible drape applied to a patient with the applicator handles being removed;

FIG. 11 is a perspective view of a third embodiment of the applicator handle showing a pair of the handles connected to the flexible bandage;

FIG. 12 is a sectional view of the drape being applied to a patient with the applicator handles of FIG. 11;

FIG. 13 is a top plan view of a sterile package containing the flexible bandage and two applicator handles; and FIG. 14 is a top plan view of a sterile package containing an applicator handle.

DETAILED DESCRIPTION

In FIGS. 1 and 3, a large area bandage, shown generally at 1, is illustrated. This bandage includes a backing 2 that has one surface coated with an adhesive 3. A nonadhesive strip 4 covers an outer edge portion of the adhesive 3 to prevent such outer edge portion from sticking to a removable liner 5, which protects the adhesive 3 until ready to use. Strip member 4 thus provides a tab section for grasping and pulling off the liner 5. Backing 2 and strip member 4 can be of a thermoplastic material, while removable liner 5 can be of a paper material. For use as a bandage, preferably the backing 2 and adhesive 3 are highly permeable to water vapor, but impermeable to liquid water and bacteria passage. Thus, a patient's covered wound, or body areas adjacent such wound, can breathe and receive oxygen through the bandage.

FIG. 2 shows the flexible bandage with the protective liner 5 removed. As shown in FIGS. 2 and 4, a rigid handle, shown generally at 7, is clamped along a left edge of the flexible bandage of FIG. 2. Also, a rigid handle 8 is clamped to the right edge portion of the flexible bandage in FIG. 2. This rigid handle, shown in FIGS. 5 and 6, can include a pair of opposed jaws 9 and 10 that are connected by a hinge portion 11. Jaws 9 and 10 can be held in clamped position by a snap latch 12. Between jaws 9 and 10 in FIG. 5 is clamped the flexible bandage, shown generally at 1.

It is acknowledged that hinged type rigid clamps with snap latches have been known and used for completely different purposes. For instance, such clamps have been used to hold upper edges of paper sheets for writing, clamp umbilical cords while they are being cut, etc. To applicants' knowledge, such a hinged clamp has never been used in a system which includes clamping an adhesive backed bandage during the application of such bandage to a patient and thereafter removal of such clamp, so as not to interfere with the flexible functioning of the bandage.

One example of the large area bandage is shown in FIG. 7 where an incise drape 15 has been secured to a patient 16. A surgical incision 17 has been made through both the drape and the patient. The water vapor permeable and liquid and bacteria impermeable incise drape protects the patient from contamination adjacent the surgical wound.

In a second embodiment of the applicator handle shown in FIGS. 8 and 9, a rigid rectangular handle 19 is attached along one edge of a flexible bandage 20. A similar applicator handle 21 is attached to an opposite edge. It should be noted that in FIG. 8 the applicator handles are along the longer edges of a rectangular bandage, whereas in FIG. 2 the handles are along the shorter edges of a rectangular bandage. The application handles could be placed in either of these locations. In the enlarged sectional view of FIG. 9, the rectangular tubular handle 19 has an adhesive coating 23 on one surface that is temporarily protected by a removable liner 24. In FIG. 8, this liner 24 has been removed and the adhesive 23 has been secured to flexible drape 20.

When the adhesive backed flexible drape is applied to a patient, a patient's anatomy often has various curved configurations. As shown in FIG. 10, the flexible bandage with a backing 25 and adhesive 26 has been attached to a patient, shown schematically in section at 27. Strip members 28 and 29 prevent the outermost edges of the bandage from adhering to the patient, thus making convenient tabs for grasping when removing the bandage from the patient. After the bandage has been applied to the patient, the rectangular tubular handles 19 and 21 are peeled from the back of the flexible bandage. This can be done by a rotating action.

FIG. 11 shows still another embodiment in which the flexible bandage 31 is secured to opposed applicator handles 32 and 33, which are shown with flattened lower edges secured to bandage 31 by adhesive. The applicator handles of FIG. 11 are formed of extruded tubing which can be somewhat flexible or bendable (although stiffer than the flexible bandage). Thus, as in FIG. 12, when the flexible bandage is applied to a patient, handles 32 and 33 can temporarily conform to the patient's anatomy when sticking down the bandage. Handles 32 and 33 would be removed from such flexible bandage after the application step so as not to interfere with the flexible functioning of the bandage 31.

The flexible bandage and applicator handles can be packaged together in a sterile package such as 35 in FIG. 13. Here flexible bandage 36 is packaged with applicator handles 37 and 38. These handles 37 and 38 can be either preattached to the flexible drape 36 or merely contained in the same package for connection to such bandage at the time of application to a patient. Alternatively, a sterile package 39 could contain one or more applicator handles, such as 40, for subsequent combining with a separate bandage.

Throughout the specification and claims the term "bandage" has been used in a broad sense to include various types of dressings and drapes which are adhesively applied to a patient.

In the above description, specific examples have been used to describe the invention. However, it is understood by those skilled in the art that certain modifications can be made to these examples without departing from the spirit and scope of the invention.

We claim:

1. In a system for bandaging a patient, said system comprising a flexible, rectangular bandage having a transparent backing with an adhesive on one surface for applying to a patient, and a removable liner protecting the adhesive prior to use; said bandage being permeable to water vapor, but impermeable to liquid water and bacteria; wherein the improvement comprises:
a first and second handle being substantially less flexible than said bandage, and attached to said bandage such that the handles maintain said bandage in a generally flat configuration and control wrinkling during handling and application of the bandage to the patient; said bandage and handles being in a sterility protecting package.

2. The system for bandaging a patient as set forth in claim 1, wherein the handles are adhesively attached to the flexible backing.

3. The system for bandaging a patient as set forth in claim 2 wherein the handles are attached on the surface of the backing opposite the surface containing the adhesive.

4. The system for bandaging a patient as set forth in claim 2 wherein the handles are attached on the surface of the backing containing the adhesive.

5. The system for bandaging a patient as set forth in claim 1, wherein the handles are attached to opposed edge areas of said bandage.

6. The system for bandaging a patient as set forth in claim 5 wherein the backing has graspable edge areas on two opposed edges thereof which are adapted not to adhere to a patient when the bandage is applied thereto; and said handles are adhesively secured to said graspable edge areas.

7. A method of bandaging a patient with the flexible bandage of claim 1 comprising the steps of:
(a) removing the protective liner from the adhesive;
(b) applying the bandage to the patient while the handles are secured to the bandage; and
(c) separating the handles from the bandage so that the handles do not interfere with the flexible functioning of the bandage on the patient's anatomy.

* * * * *